(12) United States Patent
Grotta et al.

(10) Patent No.: US 6,503,915 B2
(45) Date of Patent: Jan. 7, 2003

(54) COMPOSITION AND METHOD FOR TREATMENT OF CEREBRAL ISCHEMIA

(75) Inventors: James Grotta, Bellaire, TX (US); Roger Strong, Humble, TX (US); Jaroslaw Aronowski, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/140,703

(22) Filed: May 8, 2002

(65) Prior Publication Data

US 2002/0137758 A1 Sep. 26, 2002

Related U.S. Application Data

(62) Division of application No. 09/552,924, filed on Apr. 20, 2000.
(60) Provisional application No. 60/131,166, filed on Apr. 27, 1999.

(51) Int. Cl.[7] .................................................. A01N 43/90
(52) U.S. Cl. .................. 514/263.31; 514/724; 514/922; 514/2; 514/161; 514/165
(58) Field of Search ................................ 514/263.32, 2, 514/724, 161, 165, 922

(56) References Cited

U.S. PATENT DOCUMENTS

| | | | |
|---|---|---|---|
| 3,777,652 A | 12/1973 | Engel | 99/275 |
| 4,778,810 A | 10/1988 | Wenig et al. | 514/263 |
| 5,248,678 A | * 9/1993 | Costa et al. | 514/220 |
| 5,571,840 A | 11/1996 | Mayor et al. | 514/567 |
| 5,827,832 A | 10/1998 | Sandage, Jr. et al. | 514/49 |
| 6,166,025 A | 12/2000 | Harding et al. | 514/264 |

* cited by examiner

*Primary Examiner*—Frederick Krass
(74) *Attorney, Agent, or Firm*—Gardere Wynn Sewell LLP; Sanford E. Warren, Jr.; Thomas C. Wright

(57) ABSTRACT

A composition and method for the treatment of cerebral ischemia is disclosed, the composition is a mixture of caffeine and alcohol and is used to treat cerebral ischemia by administering to a subject in need thereof a dose of an effective amount of caffeine and at least a effective amount of an alcohol or mixtures thereof.

21 Claims, 1 Drawing Sheet

COMPOSITION AND METHOD FOR TREATMENT OF CEREBRAL ISCHEMIA

This Application is a Divisional Application of co-pending U.S. patent application Ser. No. 09/552,924 filed with the United States Patent and Trademark Office on Apr. 20, 2000, entitled A COMPOSITION AND METHOD FOR TREATMENT OF CEREBRAL ISCHEMIA. This application claims priority to the U.S. Provisional Patent Application Serial No. 60/131,166 filed on Apr. 27, 1999.

TECHNICAL FIELD OF THE INVENTION

The present invention relates in general to the field of treating cerebral ischemia, and more particularly, to the use of caffeine and alcohol following a stroke to reduce cerebral infarct damage and improve the chances for complete or substantial recovery.

BACKGROUND OF THE INVENTION

Without limiting the scope of the invention, its background is described in connection with the treatment of acute strokes, as an example.

Stroke is a severe, often-catastrophic disease affecting approximately 500,000 people per year in the U.S. Present methods of treatment except thrombolysis rely on supportive measures and non-specific agents. Twenty-five to sixty percent of stroke victims experience mild to severe disability, greatly increasing the long-term health related costs with aiding these patients. Therefore, there exists a need for improved methods of treating the morbidity experienced by these patients.

While intravenous thrombolytic treatments have shown promise, they generally require intervention within three hours of a stroke. Other unproven oral drug treatments may be initiated within a 24-hour post-stroke window and may positively affect neurological outcome with continued dosage for three months after a stroke.

One such method of protecting brain tissue from cerebral infarction subsequent to ischemia is disclosed in U.S. Pat. No. 5,827,832, issued to Sandage, Jr., et al. Sandage, Jr., et al. disclose an invention directed to a method of reducing the extent of infarction, and in particular, cerebral infarction subsequent to cerebral ischemia. Citicoline is administered shortly after an ischemic episode and continuing daily treatment for up to about 30 days, and in one preferred embodiment for at least about 6 weeks. The method taught is used for the treatment of stroke and severe head trauma patients and maximizes the chances for a full or substantially full recovery of the patient. The treatment regimen disclosed, however, uses citicoline, which is an exogenous form of cytidine-5'-diphosphocholine a key intermediate in the biosynthesis of membrane phosphatidyl choline, which is of primary importance for the dynamic regulation of cellular integrity. Furthermore the treatment protocol requires continued treatment for several weeks, with increased cost and likelihood of missing important doses.

Another method for treating central nervous system ischemia is disclosed in U.S. Pat. No. 5,571,840 issued to Mayor, et al., in which a patient who has suffered an acute insult is treated by administering an effective amount of a thyroid hormone. The thyroid hormones for use with the invention, as disclosed, include levothyroxine, liothyronine, L-3,3',5'-triiodothyronine or L-3,5-diiodothyronine, or their sodium salts. The treatment as taught is applicable to the treatment of cerebral ischemia following cardiac arrest. The thyroid hormones, however, have known short and long term side-effects and must be used with great care under a physicians close supervision.

SUMMARY OF THE INVENTION

The present inventors have recognized the need for an effective and safe treatment for human stroke and other head related trauma. Except for the tissue plasminogen activator that is used in the clinic to recanalyze occluded vessels, there is no other effective treatment for management of stroke and related diseases. The present inventors have developed and are skilled in evaluating the efficacy of various experimental pharmacological therapies using a rat model for human stroke.

The present inventors have discovered that a composition that includes caffeine plus an alcohol (i.e., analkanol), and in particular ethanol, dramatically reduces brain damage following a stroke. Like results were not observed with either caffeine or ethanol alone.

More particularly, the composition and method for protecting brain tissue from cerebral ischemia of the present invention includes administering to a subject in need thereof a dose of an effective amount of caffeine and at least a effective amount of an alcohol or mixtures thereof. The mixture of alcohols may include, e.g., ethanol.

Furthermore, a composition for use in the treatment of a subject identified as having an ischemic cerebral stroke includes an effective amount of caffeine, an effective amount of an alcohol and a pharmaceutically acceptable carrier for use in treating the subject.

The composition for use with the present invention may be provided to the subject or patient in an oral, intravenous or other form that provides an effective amount of the caffeine and alcohol. The caffeine and alcohol may even be co-administered from a common source or to a common site, or be provided separately through distinct delivery sites and modes.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
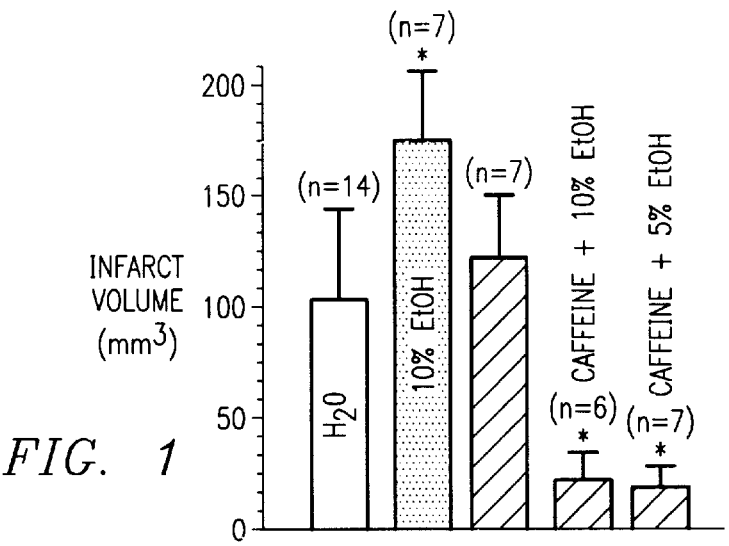
FIG. 1 is a graph showing the results obtained treating ischemic stroke orally using a composition and method according to the present invention.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

The cerebroprotective action of the composition disclosed herein was demonstrated in a rat model of transient focal cerebral ischemia in which the left middle cerebral artery (MCA) and left common carotid artery (CCA) was occluded with a stainless steel wire. Long Evans rats, weighing between 300 and 350 grams, were randomly divided into five acute treatment groups. Group 1 had fourteen animals that were orally treated with deionized water. Group 2 had seven rats orally treated with caffeine alone. Group 3 included seven rats orally treated with ethanol alone. Groups 4 and 5 were groups treated with caffeine plus ethanol, one with 10% ethanol and the second with 5% ethanol in a carrier. In the present example the carrier was water, however other pharmaceutically acceptable carriers, water-based or not, may be used with the present invention.

The animals used in these studies were generally handled as follows: briefly, the rats were anesthetized with 400 mg/kg chloral hydrate administered intraperitoneally. The left femoral artery was cannulated with PE-50 polyethylene tubing for continuous monitoring of arterial blood pressure and blood sampling for analysis of arterial blood gases, femoral vein for intravenous infusion. A small burr hole in the cranium over the ischemic cortex was produced for continuous blood flow (CBF) monitoring. Rectal temperature was maintained at 37 degrees Centigrade with a thermostatically-controlled heating lamp during the surgery and MCA occlusion.

The right MCA was accessed through a 1×2 mm burr hole made right over the MCA with a metal wire (0.005" diam.) placed below the artery. The CCA was occluded with an aneurysm clip right after the MCA was occluded.

The MCA/CCA occluders and femoral artery and vein catheter were removed after a total ischemic period of 180 minutes, permitting reperfusion of the tissue. The animals were allowed to recover from the anesthesia and to eat and drink freely.

Rats randomly received treatment either orally 3 hours and 1 hour before or by intravenous (IV infusion) for 2.5 hours beginning 30, 60, 90, 120, or 180 minutes after ischemia. Group 1 was given deionized water (dH$_2$O) orally, which served as the control group for this study. Group 2 was given caffeine orally (2×10 grams/kg). In Group 3, a solution of 10% ethanol was provided orally (2×0.65 grams/kg total). Group 4 was given, orally, 10% ethanol plus caffeine (10% ethanol at 0.65 grams/kg and 10 mg/kg caffeine), while Group 5 was given an intravenous solution of 10% ethanol (2×0.65 mg/kg) plus caffeine (2×10 mg/kg). In addition, a sixth group received, orally, 10% ethanol plus 10 mg/kg caffeine for 3 weeks prior to ischemia. After 3 hours of left MCA/CCA occlusion and 24 hour reperfusion, infarct volume was determined using 2,3,5-triphenyltetrazolium chloride. The results are described hereinbelow in association with the figures.

Control deionized (dH$_2$O) animals developed infarct volume that was 102.4+/−30.2 mm$^3$. Oral treatment with caffeine alone had no effect (122.4+/−30.2 mm$^3$) Oral ethanol alone, on the other hand, was found to exacerbate infarct volume (177.2+/−27.8 mm$^3$). Interestingly, oral caffeine plus ethanol almost entirely eliminated the damage (17.89+/−10.41 mm$^3$) When intravenous treatment with ethanol plus caffeine was initiated at 30, 60, 90 and 120 minutes post-ischemia the infarct volume was reduced to 33.07+/−17.49 mm$^3$ (n=6), 58.73+/−28.28 mm$^3$ (n=6); 41.22+/−36.99 mm$^3$ (n=6) and 61.9+/−55.5 (n=9), respectively. The protective effect of intravenous ethanol plus caffeine was lost when treatment was delayed to 180 minutes post-ischemia 87.3+/−42.6 (n=8). Furthermore, chronic daily oral treatment with alcohol plus caffeine prior to ischemia eliminated the neuroprotection seen with acute treatment.

The combination of caffeine (10 mg/kg) plus ethanol (0.65 or 0.325 grams/kg) administered to rats subject to 180 min unilateral middle cerebral/common carotid artery occlusion results in a dramatic reduction of the brain damage (infarct volume).

In contrast to the combination disclosed herein, caffeine alone did not modify infarct volume while ethanol produced significant augmentation of the damage. The combination of caffeine plus ethanol was effective in ischemia prophylaxis (oral 3 and 1 hour pretreatment reduced ischemic volume) and acute treatment (intravenous infusion of the combination initiated for up to 120 min post ischemia reduced ischemic damage).

FIG. 1 shows a summary of the results obtained using the present invention in the rat model system. The present inventors have discovered that a composition that includes caffeine plus an alcohol, in particular ethanol at either 5 (0.325 grams/kg) or 10 (0.65 grams/kg) percent was able to dramatically reduce brain damage following an experimentally induced stroke as measured by infarct volume. Like results were not observed with the deionized water control, caffeine or ethanol alone.

Figure 2:
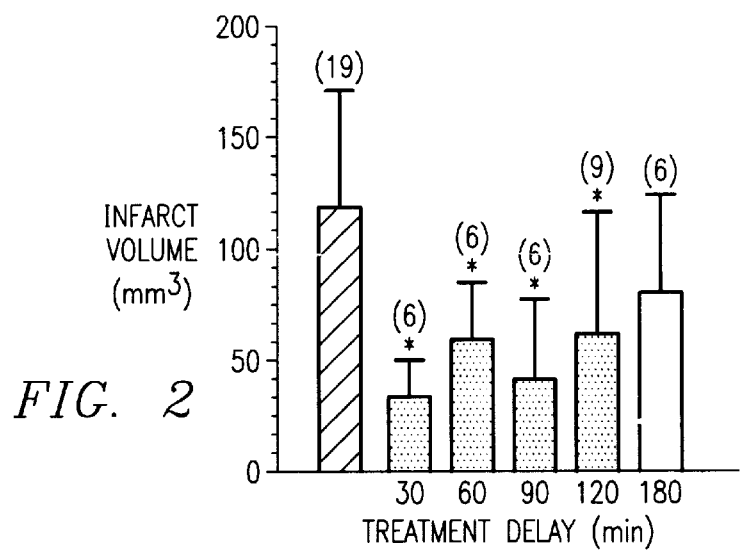
FIG. 2 is a graph showing the results obtained with intravenous treatment initiated at different time-points.

FIG. 2 shows the results obtained using the composition of the present invention in the rat model system in which the intravenous infusion of the composition was delayed. The number above each of the bars is the number of rats used in each group in the study. As can be seen, the thirty to ninety minute delay treatment period appears to help protect the animal following an occlusive event, with the 90 and 120 offering a slightly lower level of protection.

Figure 3:
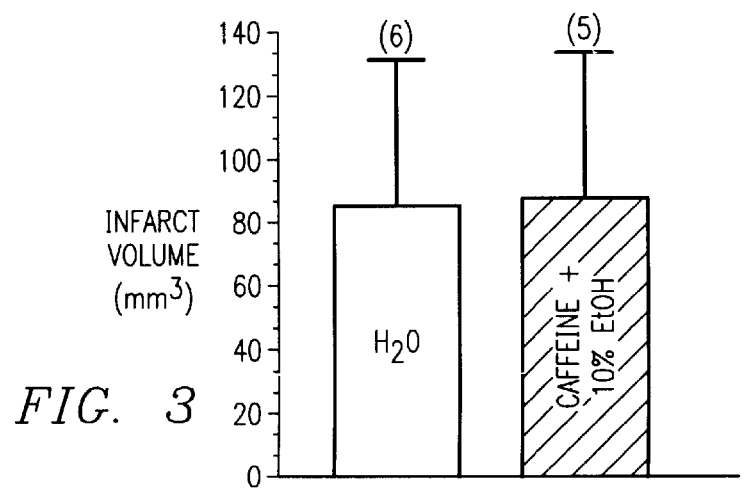
FIG. 3 is a graph showing that chronic oral pretreatment with the composition of the invention prevents the protective effect observed with the acute treatment.

FIG. 3 shows the results obtained from the treatment of chronically treated rats prior to the ischemic event. Given chronic daily oral treatment with alcohol plus caffeine prior to ischemia eliminated the neuroprotection seen with 120 and 60 minutes pretreatment.

Since both caffeine and ethanol are frequently seen as a risk factor in cerebrovascular diseases the resulting neuroprotective effect of the caffeine plus alcohol composition disclosed herein was unexpected. Furthermore, no obvious mechanism of action of the combination can be predicted.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for treating ischemic cerebral trauma, the method comprising administering to a subject in need thereof a composition comprising an effective amount of caffeine and an effective amount of an alkanol.

2. The method of claim 1, wherein said alkanol is ethanol, or a mixture of ethanol and another alkanol.

3. The method of claim 1, in which said composition is administered no later than about 24 hours after the occurrence of said ischemic cerebral trauma.

4. The method of claim 1, in which said effective amount of caffeine ranges from about 100 mg to about 5000 mg.

5. The method of claim 1, in which said caffeine and said alkanol are co-administered.

6. The method of claim 1, in which the effective amount of caffeine is in the form of a pharmaceutically acceptable salt.

7. The method of claim 1, in which said administration of said composition is carried out over a period of at least about 3 days.

8. The method of claim 1, wherein said composition is administered one or more times daily over a predetermined period.

9. The method of claim 1, wherein said ischemic cerebral trauma occurs in the brain.

10. The method of claim 1, wherein the subject is human.

11. The method of claim 1, wherein the subject is a rat, further defined as a rat model for stroke.

12. The method of claim 1, wherein the subject has suffered a cerebral ischemic trauma.

13. The method of claim 1, wherein said composition further comprises a therapeutic agent selected from the group consisting of t-PA, streptokinase, urokinase, aspirin, dipyridamole, and combinations thereof.

14. A method for treating ischemic cerebral trauma, the method comprising administering to a subject in need thereof a composition comprising an effective amount of caffeine and an effective amount of ethanol.

15. The method of claim 14, wherein said composition is administered no later than about 24 hours after the occurrence of said ischemic cerebral trauma.

16. The method of claim 14, wherein said effective amount of caffeine ranges from about 100 mg to about 5000 mg.

17. The method of claim 14, wherein said composition is administered within about 12 to about 15 hours after the occurrence of said ischemic cerebral trauma.

18. The method of claim 14, whereon said caffeine and said ethanol are co-administered.

19. The method of claim 14, wherein said effective amount of caffeine is in the form of a pharmaceutically acceptable salt.

20. The method of claim 12, wherein the cerebral ischemic trauma is a head trauma.

21. The method of claim 12, wherein the cerebral ischemic trauma is a stroke.

* * * * *